US00PP12114P2

(12) United States Plant Patent
Zary

(10) Patent No.: US PP12,114 P2
(45) Date of Patent: Oct. 2, 2001

(54) FLORIBUNDA ROSE PLANT NAMED 'JACSUMRE'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/455,215

(22) Filed: Dec. 6, 1999

(51) Int. Cl.[7] ..... A01H 5/00
(52) U.S. Cl. ..... Plt./141
(58) Field of Search ..... Plt./141, 142, 146, Plt./147, 148

*Primary Examiner*—Howard J. Locker
(74) *Attorney, Agent, or Firm*—Klarquist Sparkman Campbell Leigh & Whinston, LLP

(57) ABSTRACT

A floribunda rose plant having compact, upright growth; dark green, glossy foliage; fragrant, open large flowers; and good resistance to rust and mildrew.

1 Drawing Sheet

The present invention relates to a new and distinct variety of rose plant of the floribunda class which was originated by me by crossing the variety MACrexy (U.S. Plant Pat. No. 6,713), with the variety JACale (U.S. Plant Pat. No. 5,860).

The primary objective of this breeding was to produce a new rose variety having the upright, well branched habit, free flowering ability and glossy foliage of the female parent combined with the large flowers, fragrance and high centered flower form of the male parent. The objective was substantially achieved, along with other desirable improvements, as evidenced by the following unique combination of characteristics that are outstanding in the new variety and that distinguish it from its parents, as well as from all other varieties of which I am aware:

1. Compact, upright growth;
2. Large, open flowers;
3. Dark green, glossy foliage;
4. Fragrant flowers;
5. Good disease resistance; and
6. Novel blend of colors.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:
*Seed parent.*—MACrexy (U.S. Plant Pat. No. 6,713).
*Pollen parent.*—JACale (U.S. Plant Pat. No. 5,860).
Classification:
*Botanical.*—*Rosa hybrida.*
*Commercial.*—Floribunda.

FLOWER

Observations made from specimens grown in a garden environment at Somis, Calif. from March 1998 to August 1999.

Blooming habit: Continuous.
Bud:
*Size.*—About 1¼ inches long when the petals start to unfurl.
*Form.*—The bud form is long; pointed ovoid.
*Color.*—When sepals first divide, bud color is Orange Group 29D on the upper ⅔ of the bud with Yellow-Orange Group 22D near the base of the bud. When half blown, the upper sides of the petals are Orange-Red Group 33D except near the petal base where it is Yellow Group 11B; and the lower sides of the petals are Orange Group 29D on the petal edges and then Yellow Group 11C except for a Yellow Group 12C color spot at the base of a petal.
*Sepals.*—Color: Green Group 138B except when exposed to bright sun, when there is a blush of Greyed-Purple Group 184B. Surface texture: Covered in fine hairs. There are three lightly appendaged sepals. There are two unappendaged sepals with hairy edges.
*Receptacle.*—Color: Green Group 137B. Shape: Funnel. Size: Medium (about ¼ inch×3/16 inch). Surface: Smooth.
*Peduncle.*—Length: Medium (about 2½ to 3 inches). Surface: Smooth; with some glands. Color: Green Group 137B except when exposed to bright sunlight. Then the color is Greyed-Purple Group 183A. Strength: Stiff; erect.
Bloom:
*Size.*—Large. Average open size is four inches.
*Borne.*—Singly and several together in rounded clusters of three to five blooms.
*Stems.*—Strength: Strong. Average length is about 14 to 18 inches.
*Form.*—When first open: High centered. Permanence: Flattens; outer petals curl back.
*Petalage.*—Number of petals under normal conditions: 25 to 30.
*Color.*—The upper sides of the petals are Orange-Red Group 33D except near the petal base where they are Yellow Group 11B. The reverse sides of the petals are Orange Group 29D on the petal edge and then Yellow Group 11C. The base of each petal has on the upper surface a 3/16 inch×3/16 inch Yellow Group 13C color spot, while on the lower surface there is a slightly smaller color spot that is Yellow Group 12C. The major color on the upper side is Orange-Red Group 33D.

*Variegations.*—There are occasionally greenish-white streaks on the guard petal midrib.

*Discoloration.*—The general tonality at the end of the first day: No change. At the end of the third day: No change. By day five or six on the plant the flowers will fade on the petal edges to Orange Group 29D. By day six or seven petal drop has occured.

*Fragrance.*—Moderate; sweet damask.

Petals:

*Texture.*—Thick.

*Shape.*—Deltoid.

*Form.*—Tips slightly recurved; edges slightly quilled.

*Arrangement.*—Imbricated. Petaloids in the center are few. They are the same color as petals but vary in size from ¼ to ½ inch long and ⅛ to ¼ inch wide. They numbered from three to five in ten flowers sampled.

*Persistence.*—Petals drop off cleanly before drying.

*Lastingness.*—On the plant: Long (about seven days). As a cut flower: Long (about nine days).

Reproductive parts:

*Anthers.*—Size: Medium. Quantity: Many. Color: Yellow-Orange Group 20B. Arrangement: Regular around styles.

*Filaments.*—Color: Yellow-Orange Group 21 B.

*Pollen.*—Present.

*Styles.*—Color: Green-White Group 157D.

*Stigmas.*—Color: Yellow-White Group 158B.

Plant:

*Form.*—Bush.

*Growth.*—Vigorous; upright; branching. At maturity, height is 3½ feet, width is 2½ feet.

Foliage: Number of leaflets on normal mid-stem leaves: five.

*Size.*—Large 5½ inches long×4 inches wide).

*Quantity.*—Abundant.

*Color.*—New foliage: Upper and lower surfaces: Greyed-Purple Group 183A. Old foliage: Upper surface: Green Group 136A. Lower surface: Green Group 139B.

Leaflets:

*Shape.*—Pointed oval.

*Texture.*—Leathery; glossy.

*Edge.*—Serrated.

*Serration.*—Single; small.

*Petiole rachis.*—Color: Upper: Green Group 137A. Lower: Green Group 137B.

*Petiole underside.*—Smooth; with occasional prickles.

*Stipules.*—Short (about ½ inch long); serrated; bearded.

*Disease resistance.*—Resistant to mildew and rust; susceptilble to blackspot under normal growing conditions.

Wood:

*New wood.*—Color: Greyed-Purple Group 183B. Young wood is often Greyed-Purple Group 187A if exposed to bright sunlight. Bark: Smooth.

*Old wood.*—Color: Green Group 137A. Bark: Smooth.

Prickles:

*Quantity.*—On main canes from base: Ordinary. On laterals from main canes: Ordinary.

*Form.*—Medium; straight to hooked slightly downward.

*Color when young.*—Greyed-Purple Group 187A.

*Color when Mature.*—Greyed-Orange Group 177A.

Small prickles:

*Quantity.*—On main stalks: None. On laterals: None.

I claim:

1. A new and distinct variety of rose plant of the floribunda class, substantially as herein shown and described, characterized particularly by its compact, upright growth; dark green, glossy foliage; fragrant, open large flowers; and good resistance to rust and mildew.

* * * * *

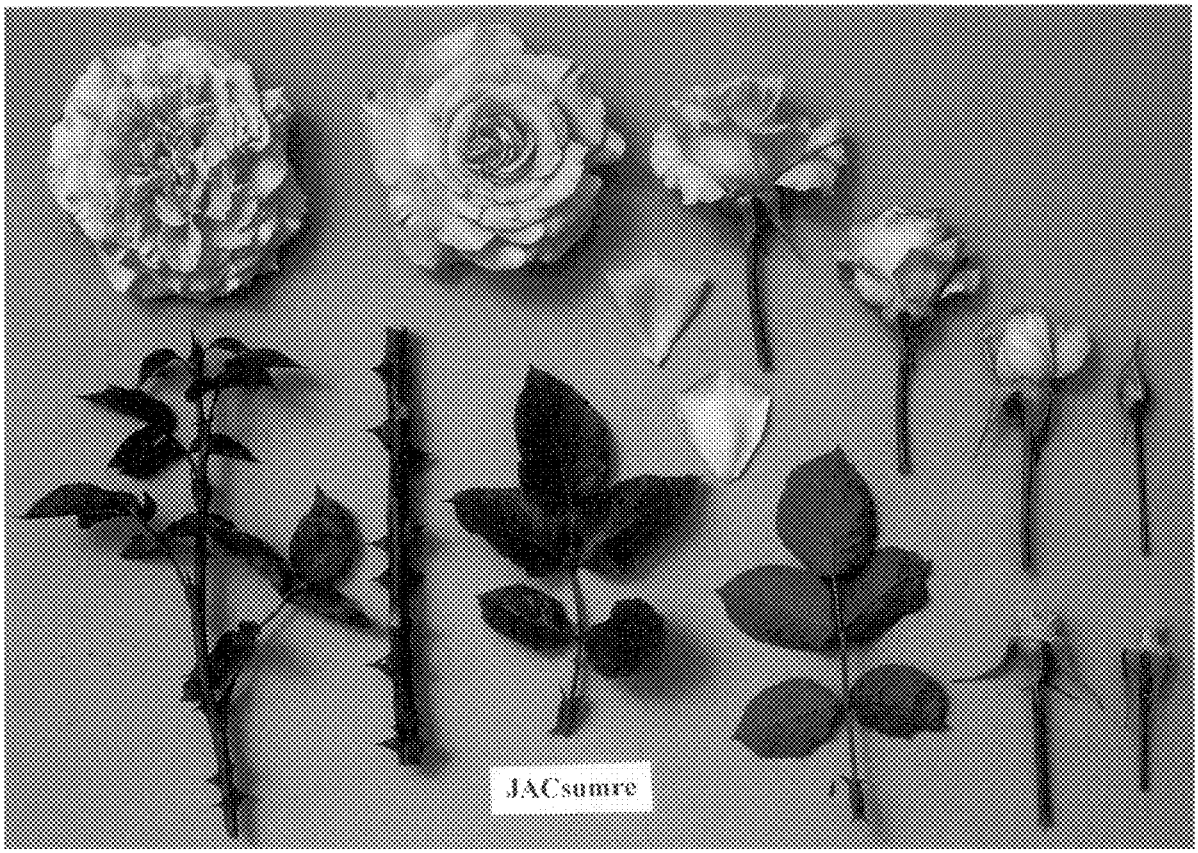
JACsumre